United States Patent [19]
Aikus et al.

[11] Patent Number: 5,498,396
[45] Date of Patent: Mar. 12, 1996

[54] SOLUTION STERILIZATION SYSTEM

[75] Inventors: Albert J. Aikus, Lake Villa, Ill.; James T. Renick, Bristol, Wis.

[73] Assignee: Abbott Laboratories, Abbott Park, Ill.

[21] Appl. No.: 332,006

[22] Filed: Oct. 31, 1994

[51] Int. Cl.$^6$ .............................. A61L 2/00; G05D 7/00; G05D 23/00
[52] U.S. Cl. .................. 422/109; 422/110; 422/115; 422/308; 99/470; 165/65
[58] Field of Search .................. 422/1, 38, 109, 422/110, 114, 115, 307, 308, 33; 137/487.5; 426/521, 522; 99/470; 165/65, 66

[56] References Cited

U.S. PATENT DOCUMENTS

| | | | |
|---|---|---|---|
| 1,745,906 | 2/1930 | O'Connell et al. | 422/1 |
| 3,285,157 | 11/1966 | Smith, Jr. | 99/470 |
| 4,584,932 | 4/1986 | Abma | 99/470 |
| 4,637,936 | 1/1987 | White et al. | 165/65 |
| 4,830,865 | 5/1989 | McFarlane et al. | 426/521 |
| 4,857,181 | 8/1989 | Shouldice et al. | 210/87 |
| 5,223,217 | 6/1993 | Frizziero | 422/26 |
| 5,288,471 | 2/1994 | Corner | 422/307 |
| 5,309,191 | 5/1994 | Bartell et al. | 354/299 |
| 5,389,335 | 2/1995 | Charm et al. | 422/307 |

FOREIGN PATENT DOCUMENTS 0428009  5/1991  European Pat. Off. .................. 422/1

*Primary Examiner*—James C. Housel
*Assistant Examiner*—Theresa T. Snider
*Attorney, Agent, or Firm*—Thomas M. Breininger; Brian R. Woodworth

[57] ABSTRACT

A sterilization system for sterilizing a solution such as a parenteral solution or diluent generally includes an arrangement for supplying a solution to be sterilized from an associated source, at least one first heat-exchanger for elevating the temperature of the solution, and at least one second heat-exchanger for subsequently cooling the solution. The system further includes an arrangement for pressurizing the system with sterile gas which is used to effect "dry-start up" of the system and to shut-down the system to minimize product losses.

12 Claims, 4 Drawing Sheets

SOLUTION STERILIZATION SYSTEM

TECHNICAL FIELD OF THE INVENTION

The present invention relates to a sterilization system for sterilizing a solution such as parenteral solutions or diluents, that can be pressurized with sterile gas prior to the initiation of sterilization of the solution to facilitate highly efficient operation of the system.

BACKGROUND OF THE INVENTION

In-line liquid sterilizers have commonly been used in the food industry, for example, for processing dairy products. A typical in-line liquid sterilizer uses a standard water start-up/product chase method. The system is flushed using water before the initiation of sterilization of the product to remove any impurities in the system as the system is brought up to the desired operating temperature. Once the heat-exchangers of the system, typically employed for both heating and cooling, are operating at the desired temperatures, product to be sterilized is introduced to "chase" the water from the system, and product sterilization is initiated.

Inevitably, when the product is initially passed through the system, the water and product mix. Thus, initially, a large quantity of product must be discarded due to dilution by the water. After the flow of product causes the water to be completely removed, the undiluted product passes through the system and sterile product is produced.

This type of in-line liquid sterilizer is not practical for use in the pharmaceutical industry. The design does not address all pharmaceutical standards and requirements. In particular, the standard water start-up/product chase method is not advantageous for sterilization of relatively expensive pharmaceutical products since a relatively high volume of product loss during start-up typically occurs. Such systems also result in undesirably high product losses during system shut-down.

SUMMARY OF THE INVENTION

This invention provides a sterilization system for sterilizing a liquid, such as a parenteral solution or a diluent such as saline. The system may also be used to process human and animal consumables. Notably, the system can be pressurized with a sterile gas, both prior to solution sterilization, and attendant to system shut-down. Pressurization of the system with sterile gas (typically sterile air) facilitates highly efficient operation of the system by minimizing product losses during system start-up and shut-down. The system is operated to achieve sterilization while minimizing heat input, to avoid degradation of the product. The potency of the resultant product is thus optimized. This is achieved through rapid heating and cooling of the product.

In accordance with the disclosed embodiment, the present sterilization system includes an arrangement for supplying a solution from an associated source, at least one first heat-exchanger for elevating the temperature of the solution, and at least one second heat-exchanger for subsequently cooling the solution. The system further includes an arrangement for pressurizing the system with sterile gas which is used to effect "dry start-up" of the system, rather than the typical product chase method, and which is also used during system shut-down to minimize product loss.

The first heat-exchanger, for elevating the temperature of the solution, is downstream of and in fluid communication with the arrangement for supplying solution from the associated product source. The second heat-exchanger, for cooling the solution, is downstream of and in fluid communication with the first heat-exchanger. A dwell tube is interposed between and in fluid communication with the heat-exchangers.

The arrangement for pressurizing the system with sterile gas includes first and second sources of sterile gas. The first source is preferably joined in fluid communication downstream of the second heat exchanger and primarily is used during start-up of the system. The second source is preferably joined in fluid communication downstream of the first heat-exchanger and upstream of the second heat-exchanger and primarily is utilized during shut-down of the system.

During start-up of the system, the system is first purged and sterilized with high quality steam from deionized water provided by a high quality steam generator. Following steam purging and sterilization, the system then is pressurized with sterile gas from the first source of sterile gas prior to the initiation of sterilization of the solution. A dump valve releases the steam condensate when the system is being pressurized with sterile gas. The dump valve is preferably interposed between and in fluid communication with the solution source and the first heat-exchanger.

Solution to be sterilized is directed from the product source toward an air separator which is in fluid communication therewith. A blocking valve prevents the as yet non-sterilized solution from flowing to the first heat-exchanger. The blocking valve selectively starts and stops the flow of non-sterilized solution supplied from the solution source to the first heat-exchanger. The air separator releases non-sterile air from the system. Once the non-sterile air is expelled and the system is pressurized with sterile gas, the sterilization process is ready to begin.

To sterilize the non-sterilized solution, the blocking valve is opened and non-sterilized solution is supplied from the product source to the first heat-exchanger. The first heat-exchanger receives the non-sterilized solution and elevates the temperature of the solution to effect sterilization. The sterilized solution exits the first heat-exchanger through the dwell tube.

After passing through the dwell tube, the sterilized solution flows into the second heat-exchanger. The second heat-exchanger decreases the temperature of the sterilized solution before the sterilized solution is moved out of the system for subsequent packaging and/or storage.

During shut-down of the system, the arrangement for pressurizing the system with sterile gas from the second source of sterile gas functions to minimize loss of product. Specifically, the second heat-exchanger is pressurized with sterile gas, which urges the sterilized solution through this heat-exchanger and out of the system for subsequent packaging and/or storage.

The pressurizing arrangement further functions such that non-degraded solution, i.e. substantially unheated solution, is backflowed to the source. During solution backflow, degraded solution is urged from the first heat-exchanger and subsequently out the dump valve. A cooler, which is in fluid communication with the first heat-exchanger, decreases the temperature of the degraded solution when the degraded solution is backflowed to the dump valve and is passed from the system. Thus, during shut-down, product which is sterilized, as well as product which is unsterilized but non-degraded by heating, is preserved, while degraded product is moved out of the system.

A timer operates the blocking valve in timed relationship with operation of the pressurizing arrangement, so that during shut-down of the system, non-degraded solution is backflowed from the first heat-exchanger to the source. The timer thereafter operates to open the dump valve so that the pressurizing arrangement urges the degraded solution (under the influence of the pressurized sterile gas) from the first heat-exchanger and out of the system through the dump valve.

Suitable programmable logic controls are provided in the system and are used to sequence and control valves, pumps, etc. The elements of the system are coupled to the logic controls by suitable circuitry.

Thus, the present invention provides a sterilization system that is pressurized with sterile gas prior to the initiation of sterilization of a solution, desirably resulting in a smaller quantity of solution being discarded during start-up than in prior art systems. Pressurization of the system with sterile gas attendant to system shut-down also results in a smaller amount of solution being subject to loss than in prior art systems.

These and other objects, features, and advantages of this invention are evident from the following description of a preferred embodiment of this invention with reference to the accompanying drawings.

DETAILED DESCRIPTION OF THE PREFERRED EMBODIMENT

Figure 1:
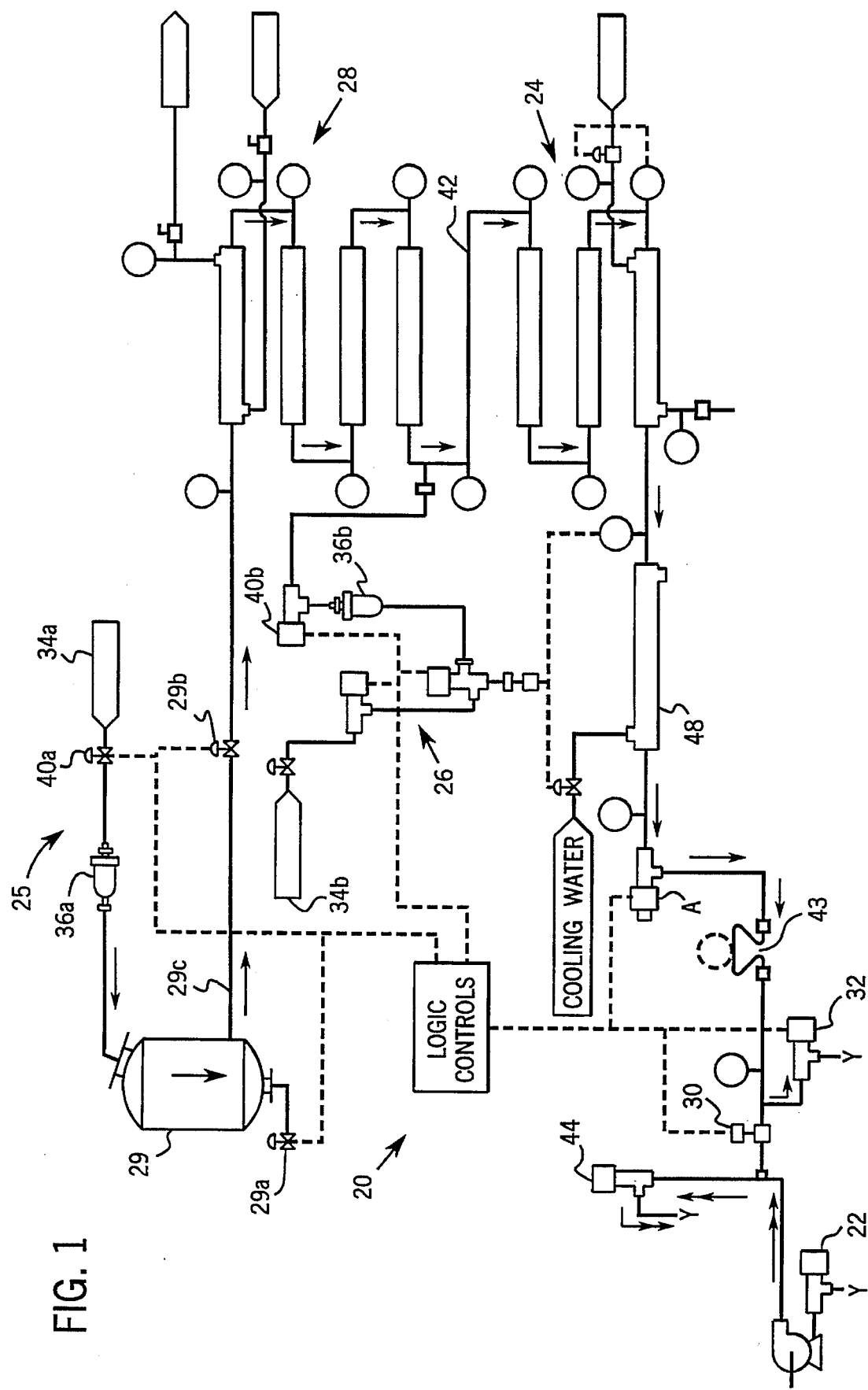
FIG. 1 is a schematic view of a solution sterilization system according to the present invention illustrating the start-up of the system, with single-headed arrows showing flow of sterile gas in the system, and double-headed arrows showing flow of solution.

While the present invention is susceptible of embodiments in various forms, there is shown in the drawings and will hereinafter be described a presently preferred embodiment, with the understanding that the present disclosure is to be considered as an exemplification of the invention, and is not intended to limit the invention to the specific embodiment illustrated.

As illustrated in the drawings, this invention provides a sterilization system 20 for sterilizing a solution. The system 20 is advantageously used for processing parenteral solutions, such as intravenous drugs, or diluents such as saline. The system 20 may also be used to process human and animal consumables.

As opposed to standard prior art water startup/product chase methods, the solution sterilization system 20 of the present invention uses a novel start-up method referred to herein as "dry start-up." Dry start-up uses a sterile gas to purge condensate from initial steam sterilization of the system and pressurize the system 20 before solution is introduced into the system 20. Thus, the prior art problem of water creating a diluted product is avoided in the present invention and less product needs to be discarded due to unacceptable dilution.

The solution sterilization system 20 of the present invention generally includes a supply arrangement 22, including a pump, for supplying a solution to the system 20 from an associated product source.

In order to purge and sterilize the system 20 prior to the present dry start-up procedure, the entire system 20 preferably is first filled or charged with high quality steam formed from deionized water provided by a high quality steam generator (not illustrated). Although the position of the steam generator can vary, it preferably is positioned at the end of the system 20 opposite the supply arrangement 22 and downstream of most if not all of the other components of the system 20.

The system 20 further includes at least one first heat-exchanger 24 for elevating the temperature of the solution for effecting sterilization. The system 20 additionally comprises first and second arrangements for pressurizing the system 20 with sterile gas, generally designated 25 and 26 respectively, at least one second heat-exchanger 28 which functions to decrease the temperature of the solution as it is directed therethrough and a sterile hold tank 29 for storing solution sterilized by the system 20. Suitable piping or conduits are used to connect the elements 22, 24, 25, 26, 28 and 29 of the system 20 so that the elements are in fluid communication with each other. Herein, these pipes or conduits will be referred to as "lines." Suitable valves, which will be described herein, are provided in the system 20 along the lines to selectively start or stop the flow of solution or gas.

Initially, the general elements of the system 20 will be described. Additional features, advantages and elements will be described in reference to the process for using the sterilization system 20.

The supply arrangement 22 pumps a solution into the system 20 from the source (not shown) so that sterilization of a solution can be effected. The solution from the supply arrangement 22 can be sterilized, such as by filtration or other method to at least minimize the bioburden, i.e., naturally occurring bacteria in the solution.

The supply arrangement 22 is downstream of the source and in fluid communication with the source. The supply arrangement 22 may include a standard pump for pumping the non-sterilized solution from the source to the heat-exchanger 24. In a current embodiment, solution is supplied at a flow rate on the order of 4 to 8 liters/minute.

A blocking valve 30 is interposed between and in fluid communication with the supply arrangement 22 and the first heat-exchanger 24 to selectively start and stop the flow of non-sterilized solution from the source and supply arrangement 22 to the heat-exchanger 24 for reasons described herein. The blocking valve 30 is of well known construction and may be air operated, such as a Model 7806-1-EC5-P3 valve, available from the Saunders Co., of Houston, Tex.

A dump valve 32 is interposed between and in fluid communication with the supply arrangement 22 and the first heat-exchanger 24. The dump valve 32 releases steam condensate provided by the steam generator, or distilled water which is used to rinse the system 20 between uses, from the system 20 prior to start-up and also releases degraded solution from the system 20 during shut-down as described herein. In a current embodiment, a Model 7806-1-EC5-P3 valve, available from the Saunders Co., of Houston, Tex., is employed.

The first heat-exchanger 24 is upstream of and in fluid communication with the second arrangement 26 for pressurizing the system with sterile gas, and downstream of and in fluid communication with the supply arrangement 22 and the non-sterilized solution source.

The first heat-exchanger 24 is used to effect sterilization of the solution.

The first heat-exchanger 24 is of a typical construction and may include a pre-heater in fluid communication, by suitable piping or conduits, with a series of individual heating elements. The pre-heater elevates the temperature of the non-sterilized solution to a predetermined temperature prior to the sterilization. The heating elements of the heat-exchanger elevate the temperature of the solution as the solution passes therethrough to effect sterilization of the solution. The heating elements and the pre-heater are preferably internally electropolished with an expansion bellows on the steam jacket, and may be steam heated.

In a current embodiment, the pre-heater of the first heat-exchanger 24 is supplied with steam at a temperature ranging from 100° to 140° C., to pre-heat and elevate the temperature of solution introduced at about 25° C. Each of the two further heating elements of the heat-exchanger 24 can be operated to create increases on the order of 120° C. in the temperature of solution directed therethrough. It is contemplated that solution will enter the pre-heater of the heat-exchanger 24 at about 25° C., and be elevated to a temperature on the order of about 60°–95° C. The flow rate from the pump of the solution supply arrangement 22, is designed to effect this increase in solution temperature in less than one minute.

The first pressurizing arrangement 25 functions to permit "dry start-up" of the system 20. As used herein, "dry start-up" means that the system 20 is pressurized with a sterile gas before the non-sterilized solution is introduced into the system 20. The use of a sterile gas (typically air) minimizes or eliminates the amount of diluted end product that is initially produced upon the start-up of the system 20. Thus, initially, less end product must be discarded. The use of a dry start-up and the subsequent reduction of product loss during processing allows the system 20 to efficiently process expensive pharmaceuticals.

The first pressurizing arrangement 25 is joined in fluid communication with and downstream of the second heat-exchanger 28. The first pressurizing arrangement 25 includes a first source of gas 34A, which may comprise air or nitrogen, at least one suitable anti-microbial filter 36a in fluid communication with the first gas source 34A and a first valve 40a.

As the gas is delivered from the first source 34a through the supply line, the filter 36a filters out the impurities in the gas to create a sterile gas. The valve 40a selectively starts or stops the flow of sterile gas into the system 20. In a current embodiment, commercially available anti-microbial filters, 0.22 micron Sealkleen filter, available from the Pall Co., of East Hills, N.Y. have been employed.

The sterile hold tank 29 is used to accumulate and/or temporarily store solution sterilized by the system 20 and preferably is positioned between the first pressurizing arrangement 25 and the second heat-exchanger 28. To remove sterilized solution from the hold tank 29, and to remove steam condensate when the hold tank is initially purged and sterilized with steam condensate prior to dry start-up, an outlet valve 29a preferably is provided proximate the bottom of the hold tank 29.

During dry start-up, the hold tank 29 preferably is purged independently from the remainder of the system 20 by opening the outlet valve 29a, closing a back-pressure valve 29b and opening valve 40a. This starts a flow of gas into the top of the hold tank 29 which forces the steam condensate out of the bottom of the hold tank 29. It is also to be noted that the hold tank 29 is connected to the remainder of the system 20 by a line 29c which preferably is connected near the bottom of the hold tank 29.

The second pressurizing arrangement 26 is joined in fluid communication with the first heat-exchanger 24 and the second heat-exchanger 28 downstream of the first heat-exchanger 24 and upstream of the second heat-exchanger 28. It is contemplated that the pressurizing arrangement 26 injects sterile gas into the system 20 at or downstream of the "sterility point," i.e. the point at which the system achieves sterility, of the solution. The sterility point can differ for different solutions. However, it is to be understood that it is believed that sterility of the solution may be achieved within the heat-exchanger 24 or at some point in the lines after the heat-exchanger 24. It is also contemplated that a sterile zone exists at all points downstream of the sterility point.

The second pressurizing arrangement 26 is similar to the first pressurizing arrangement 25 and includes a source of gas 34b, which may comprise air or nitrogen, at least one suitable anti-microbial filter 36b in fluid communication with the gas source 34b along a sterile gas supply line, and a pressurizing valve 40b. As the gas is delivered from the source 34b through the supply line, the filter 36b filters out the impurities in the gas to create a sterile gas. The pressurizing valve 40b selectively starts or stops the flow of sterile gas into the system 20. In a current embodiment, commercially available anti-microbial filters, 0.22 micron Sealkleen filter, available from the Pall Co., of East Hills, N.Y. have been employed.

The second heat-exchanger 28 is downstream of and in fluid communication with the second pressurizing arrangement 26 and the first heat-exchanger 24 and is used to decrease the temperature of the sterilized solution after the first heat-exchanger 24 has elevated the temperature of the solution. The cooling first heat-exchanger 28 may be comprised of a series of individual heat-exchanging elements with each being in fluid communication with another. The elements are of standard construction and may be water cooled. In a current embodiment, sterilized solution is cooled from about 132° C. to about 25° C., with the individual heat-exchanging elements being similar to the heat-exchange elements as described above. At the above-noted flow rate, cooling is achieved in less than one minute.

The system 20 also includes a dwell tube 42 which is interposed between and in fluid communication with the heat-exchanger 24 and the heat-exchanger 28. The dwell tube 42 is made of suitable piping or conduits.

Suitable automatic programmable logic controls (FIG. 1) are used to sequence and control valves, pumps, and other components of the system. The elements of the system 20 are coupled to the logic controls by suitable circuitry. The heat-exchangers are monitored by suitable thermocouples (not shown). Flow rate in the lines are monitored by flow metering means 43.

Having described the general elements of the system 20, the process for using the system 20 will now be described. Additional advantages and features of the general elements will become clear herein in reference to the process for using the system 20. Additional elements of the system 20, as well as the advantages and features of these additional elements, will also be described herein in reference to the process for using the system 20.

In the following description of the process for sterilizing the solution, the flow of the sterile gas is shown by single-headed arrows in the drawings. The flow of solution is shown by double-headed arrows in the drawings.

As shown in FIG. 1, to steam sterilize the system 20, a high quality steam generator (not illustrated) is operably connected to introduce steam into the system 20, such as through valve 40b, for example. During this steam sterilization, the valve 40a and blocking valve 30 are closed and the dump valve 32 is open by action of the logic controls.

Once the system is steam sterilized for a desired period of time, the outlet valve 29a is closed and the valve 40a is opened. This enables the first pressurizing arrangement 25 to dry start the system 20 prior to the initiation of sterilization of the solution by pumping sterile gas into the system 20. The sterile gas is pumped into the system 20 at approximately 70 psi. The first and second heat-exchangers 24 and 28 are activated by the automatic logic controls. During this pressurization, the blocking valve 30 remains closed, a back-pressure valve "A" is opened slightly, thereby throttling gas flow therethrough and maintaining pressure in the system downstream of the back-pressure valve "A", and the dump valve 32 remains open by action of the logic controls.

When the system 20 is pressurized, any fluids that have accumulated in the lines are purged from the lines and out of the system 20. The line between the closed blocking valve 30 and the dump valve 32 will be flushed with the sterile gas when the sterile gas pressurizes the system 20.

The dump valve 32 releases any residual liquid, such as steam condensate, as well as any gas from the system 20 when the system 20 is pressurized. Once it is determined that the system has been completely flushed with the sterile gas, the system 20 is ready to process solution. The quality of sterility of the gas may be measured by well known means.

Also during start-up, as shown in FIG. 1, non-sterilized solution is flowed toward an air separator 44 by action of the solution supplying arrangement 22. This acts to flush and purge any accumulated non-sterile air from the line. The air separator 44 is in fluid communication with the supply arrangement 22 by suitable piping or conduits. The blocking valve 30 is closed and prevents the non-sterilized solution from flowing to the heat-exchanger 24 during pressurization (i.e. purging) of the system 20. The air separator 44 releases any accumulated non-sterile air from the line. Once the non-sterile air is completely expelled upstream of valve 30 the system 20 is pressurized with sterile gas and the system 20 is ready to sterilize solution.

Before product sterilization, the flow of sterile gas from the first pressurizing arrangement 25 is stopped by closing dump valve 32. The dump valve 32 is closed and the blocking valve 30 as well as the back-pressure valve 29b are opened while the back-pressure valve "A" remains slightly open for throttling solution therethrough. The valves "A", 29b, 30 and 32 are opened or closed by the logic controls.

As the solution flows into the system 20 for sterilization, a gas/liquid interface passes through the system 20 from the back-pressure valve "A" to the back-pressure valve 29b. Once the gas/liquid interface passes the back-pressure valve 29b, the logic controls initiate slow, systematic closing of back-pressure valve 29b, preferably within about 40 seconds, and full opening of back-pressure valve "A". This transfers control or throttling of liquid flow through the system 20 from the back-pressure valve "A" to the back-pressure valve 29b.

Figure 2:
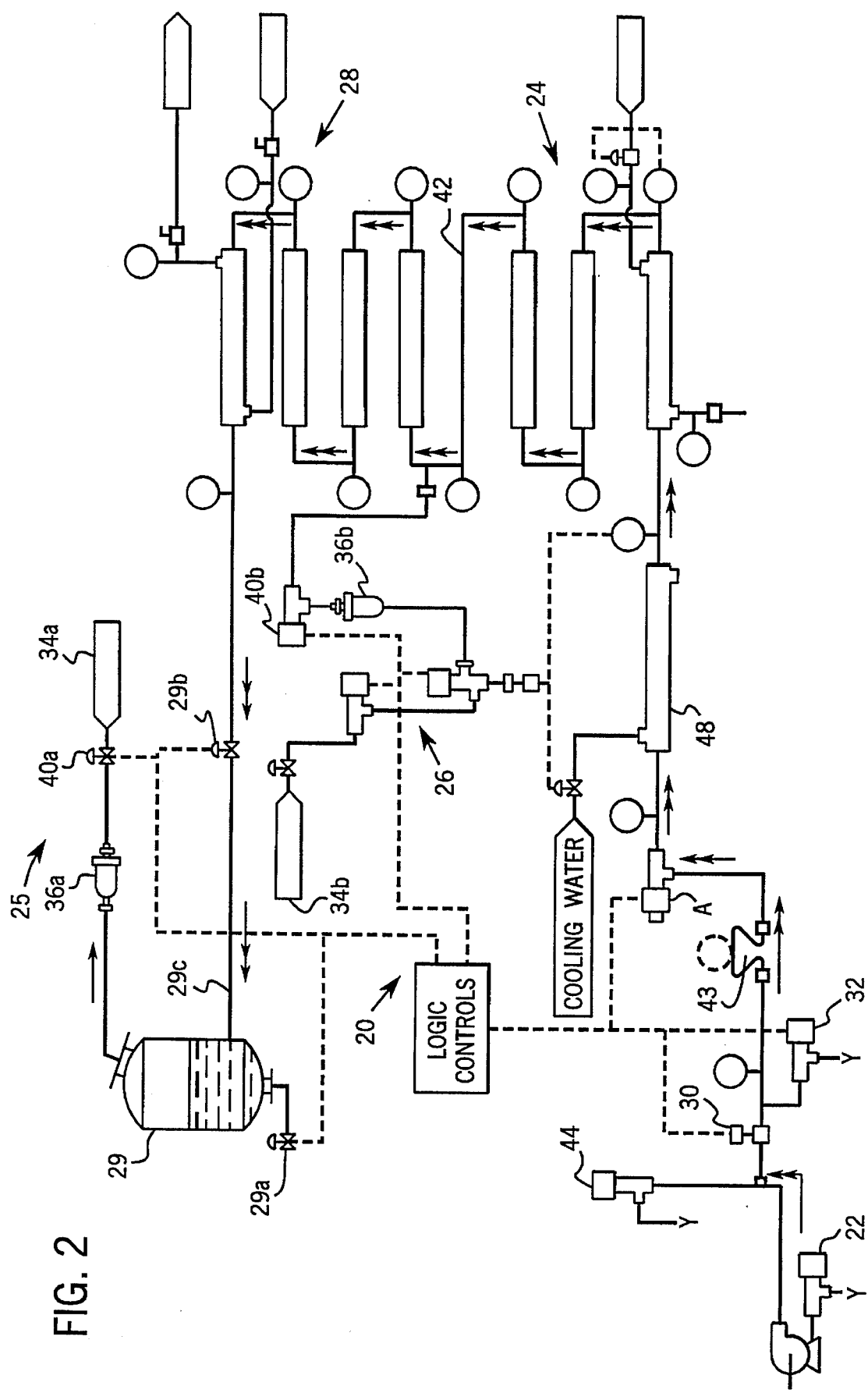
FIG. 2 is a schematic view of the system shown in FIG. 1 illustrating the flow of solution through the system.

To sterilize the solution, as shown in FIG. 2, the supply arrangement 22 supplies a flow of non-sterilized solution from the source through the back-pressure valve "A" and to the first heat-exchanger 24. To avoid substantial degradation and to minimize the potency loss of the sterilized solution, the solution is rapidly heated and cooled by the first heat-exchanger 24 and the second heat-exchanger 28, respectively, to achieve the requisite thermal input. The system is preferably pressurized during sterilization, to at least 50 psi, to avoid vaporization of solution.

The first heat-exchanger 24 receives the non-sterilized solution and elevates the temperature of the solution to effect sterilization. The system 20 operates at elevated temperatures, in conjunction with control of flow through the system, to effect controlled and measured heating of solution through precise measurements of temperature and time. The heat transferred into the solution emitted from the first heat-exchanger 24 is monitored by suitable thermocouples. Solution attributes are taken into account to assure precise determination of thermal input. During sterilization, the solution will inevitably partially degrade, i.e. lose potency, as the solution is subjected to these elevated temperatures. However, the overall product loss and product potency loss are minimized in the system 20 as compared to the losses that occur in prior art systems. Furthermore, the system 20 may be used for the sterilization of heat sensitive drugs which cannot be terminally sterilized by conventional means.

After the solution passes through the first heat-exchanger 24, the solution passes through the dwell tube 42. After passing through the dwell tube 42, the sterilized solution flows into the second heat-exchanger 28. The second heat-exchanger 28 decreases the temperature of the sterilized solution before the sterilized solution is expelled from the system 20. The temperature of the second heat-exchanger 28 is monitored by suitable thermocouples. During sterilization of solution, a constant flow rate is preferably maintained throughout the system 20.

Figure 3:
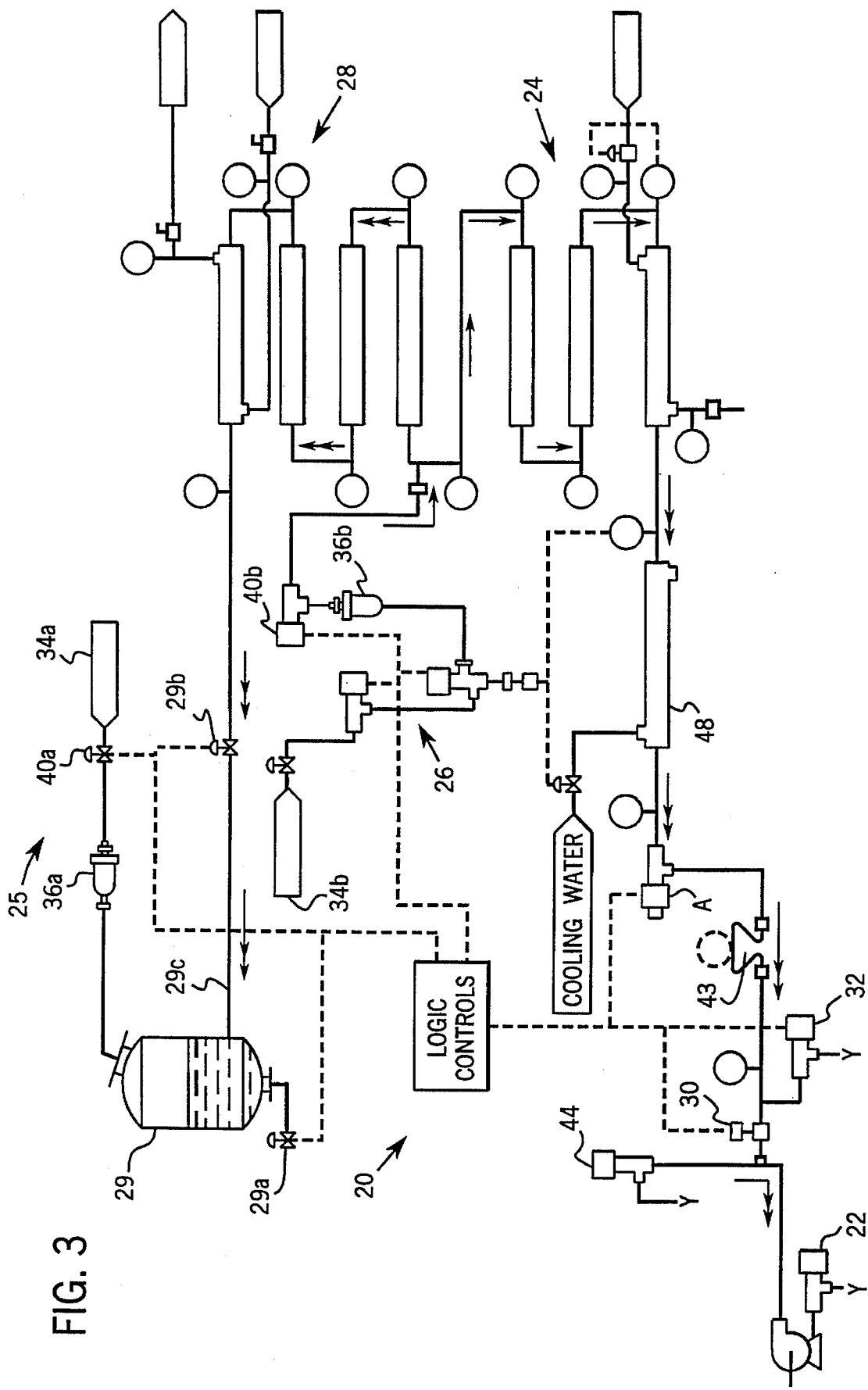
FIG. 3 is a schematic view of the system shown in FIG. 1 illustrating a phase of the shut-down of the system.
Figure 4:
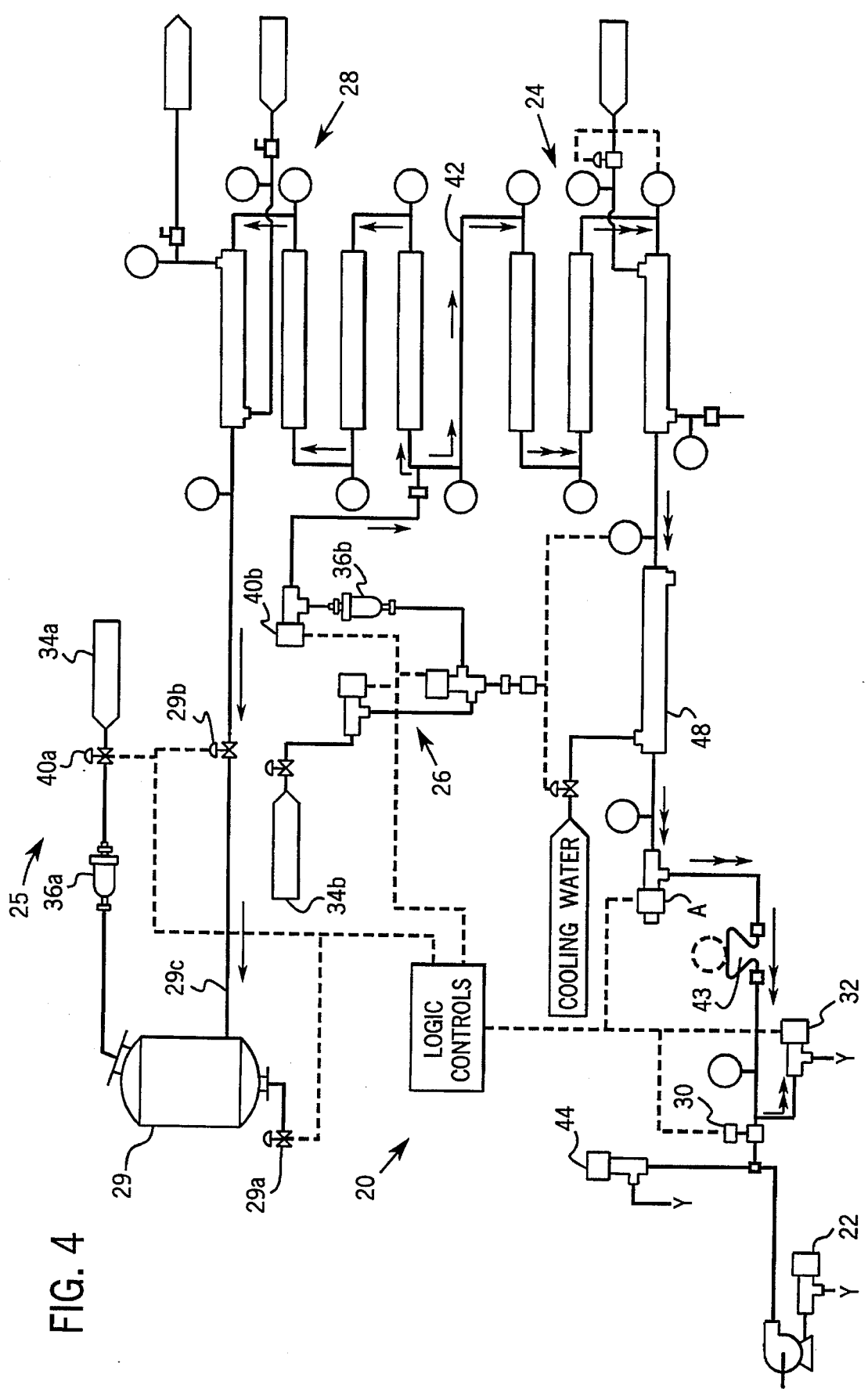
FIG. 4 is a schematic view of the system shown in FIG. 1 illustrating another phase of the shut-down of the system.

As shown in FIGS. 3 and 4, during shut-down of the system 20, the second pressurizing arrangement 26 repressurizes the system 20 with sterile gas in order to move sterile solution out of the system, as well as to preserve solution which has not yet been sterilized and which is not unacceptably degraded by heating. During shut-down of the system 20, the first heat-exchanger 24 and second heat-exchanger 28 may be deactivated by the automatic logic controls, or may be operated at a reduced steam pressure and temperature.

Initially, as shown in FIG. 3, the dump valve 32 is closed and the blocking valve 30 and pressurizing valve 40b are opened by action of the logic controls. The second pressurizing arrangement 26 pumps sterile gas into the system 20 to purge the non-sterilized solution, the degraded solution and the sterilized solution as described hereinbelow. Specifically, the deactivated second heat-exchanger 28 is pressurized with sterile gas, which urges the sterilized solution which has accumulated therein through the second heat-exchanger 28 so that it may be collected in the sterile hold tank 29. Pressurization of the first heat-exchanger 24 causes non-degraded solution to be backflowed to the product source. The point at which significant degradation occurs in the line will differ for different products.

The logic controls operate the blocking valve 30 in timed relationship with operation of the second pressurizing arrangement 26, so that during shut-down of the system 20, non-degraded solution is backflowed through the line from the first heat-exchanger 24 to the source. The logic controls operate to close blocking valve 30 and to open the dump valve 32, as shown in FIG. 4, so that the second pressurizing arrangement 26 urges degraded solution from the first heat-exchanger 24 and out of the system 20 through the dump valve 32.

A cooler 48 (i.e., a heat-exchanger), which is upstream of and in fluid communication with the first heat-exchanger 24, is activated during shut-down by the automatic logic controls and decreases the temperature of the degraded solution (typically cooling the solution from about 132° C. to about 82° C.) as the degraded solution is backflowed through the system 20 for expulsion through the dump valve 32. The cooler 48 is of a standard construction and may be water cooled.

After the sterilized solution, non-degraded solution and degraded solution have been purged and evacuated from the system 20, the cooler 48 upstream of the first heat-exchanger 24 is deactivated, and a dry start-up can be effected as described hereinabove in reference to FIG. 1. Thereafter, the system 20 is ready to resume sterilization of solution as described hereinabove in reference to FIG. 2.

Alternatively, after purging of the sterilized, non-degraded and degraded solutions from the system 20, the system 20 can first be cleaned with rinse water, such as distilled water or the like, and then sterilized with high quality steam as described above prior to initiating another dry start-up. It also is to be noted that, if desired, the pressurizing arrangement 25 can independently provide dry start-up of the system 20.

From the foregoing, it will be observed that numerous modifications and variations can be effected without departing from the true spirit and scope of the novel concept of the present invention. It is to be understood that no limitation with respect to the specific embodiment is intended or should be inferred. The disclosure is intended to cover by the appended claims all such modifications as fall within the scope of the claims.

What is claimed is:

1. A solution sterilization system comprising:
    first heat-exchanger means having a capacity to receive a solution, to increase a temperature of said solution, and to sterilize said solution by heat sterilization;
    supply means for supplying said solution to said first heat-exchanger means, said supply means being in fluid communication with said first heat-exchanger means: and
    means for pressurizing said system, said means for pressurizing having a capacity to backflow said solution from said heat-exchanger means to said supply means.

2. A solution sterilization system as defined in claim 1, said system further comprising second heat-exchanger means in fluid communication with said first heat-exchanger means at a position distal said supply means, said second heat-exchanger means having a capacity to decrease said temperature of said solution after said temperature of said solution is elevated by said first heat-exchanger means.

3. A solution sterilization system as defined in claim 2, further including dwell tube means interposed in fluid communication between said first and second heat-exchanger means.

4. A solution sterilization system as defined in claim 2, said system further comprising a conduit in fluid communication with said first heat-exchanger means and said second heat-exchanger means, said conduit having a capacity to receive said solution from said first heat-exchanger means and to transport said Solution to said second heat-exchanger means, and wherein said means for pressurizing said system has a capacity to flow said solution through said second heat-exchanger means and out of said system.

5. A solution sterilization system as defined in claim 1, said system further comprising valve means for selectively releasing said solution from said system, said valve means being positioned within said supply means.

6. A solution sterilization system as defined in claim 1, said system further comprising control means for selectively operating said valve means and said pressurizing means.

7. A solution sterilization system as defined in claim 1, said system further comprising cooling means for cooling said solution in said supply means during backflow of said solution.

8. A solution sterilization system as defined in claim 1, said system further comprising air separator means for releasing gases from said supply means before said solution is supplied to said first heat-exchanger means, said air separator means in fluid communication with said supply means.

9. A solution sterilization system as defined in claim 1, said system further comprising valve means in fluid communication with said supply means and said first heat-exchanger means, said valve means having a capacity to control selectively flow of said solution from said supply means to said first heat-exchanger means.

10. A solution sterilization system comprising:
    first heat-exchanger means having a capacity to receive a solution, to increase a temperature of said solution, and to sterilize said solution by heat sterilization;
    supply means for supplying said solution to said first heat-exchanger means, said supply means being in fluid communication with said first heat-exchanger means;
    second heat-exchanger means in fluid communication with said first heat-exchanger means at a position distal said supply means, said second heat-exchanger means having a capacity to decrease said temperature of said solution after said temperature of said solution is elevated by said first heat-exchanger means;
    valve means for selectively releasing said solution from said system, said valve means being positioned within said supply means;
    first means for pressurizing said system in fluid communication with said system at a position downstream of both of said first and second heat-exchanger means; and
    second means for pressurizing said system in fluid communication with said system at a point intermediate said first heat-exchanger means and said second heat-exchanger means;
    said first means for pressurizing said system being operable to pressurize said system prior to supplying said solution from said supply means to said first heat-exchanger means, said first means for pressurizing said system having a capacity to force liquids and gases within said system through said valve means; and
    said second means for pressurizing said system being operable during shut-down of said system, said second pressurizing means having a capacity to backflow said solution from said first heat-exchanger means to said supply means.

11. A solution sterilization system as defined in claim 10, said system further comprising control means for selectively operating said valve means, said first means for pressurizing said system, and said second means for pressurizing said system.

12. A solution sterilization system as defined in claim 11, said system further comprising cooling means for cooling said solution in said supply means.

* * * * *